(12) United States Patent
Chaim

(10) Patent No.: US 12,144,721 B2
(45) Date of Patent: Nov. 19, 2024

(54) IMPLANTABLE NIPPLE

(71) Applicant: FIXNIP LTD., Even Yehuda (IL)

(72) Inventor: Yagil Netta Chaim, Even Yehuda (IL)

(73) Assignee: FIXNIP LTD., Even Yehuda (IL)

( * ) Notice: Subject to any disclaimer, the term of this patent is extended or adjusted under 35 U.S.C. 154(b) by 554 days.

(21) Appl. No.: 17/611,941

(22) PCT Filed: May 19, 2020

(86) PCT No.: PCT/IL2020/050544
§ 371 (c)(1),
(2) Date: Nov. 17, 2021

(87) PCT Pub. No.: WO2020/234872
PCT Pub. Date: Nov. 26, 2020

(65) Prior Publication Data
US 2022/0226102 A1    Jul. 21, 2022

Related U.S. Application Data

(60) Provisional application No. 62/850,555, filed on May 21, 2019.

(51) Int. Cl.
*A61F 2/12*    (2006.01)
*A61F 2/00*    (2006.01)

(52) U.S. Cl.
CPC ........ *A61F 2/12* (2013.01); *A61F 2002/0081* (2013.01); *A61F 2210/0014* (2013.01); *A61F 2220/0033* (2013.01); *A61F 2250/0003* (2013.01)

(58) Field of Classification Search
None
See application file for complete search history.

(56) References Cited

U.S. PATENT DOCUMENTS

| 4,778,465 | A | 10/1988 | Wilkins | |
|---|---|---|---|---|
| 2011/0247636 | A1* | 10/2011 | Pollack | A61F 15/008 128/890 |
| 2012/0143330 | A1 | 6/2012 | Linares | |
| 2014/0309737 | A1 | 10/2014 | Kullas et al. | |
| 2017/0065404 | A1 | 3/2017 | Netta Chaim et al. | |
| 2020/0324021 | A1* | 10/2020 | Van Belleghem | A61L 27/26 |
| 2021/0121317 | A1* | 4/2021 | Bronnimann | A61F 5/449 |

FOREIGN PATENT DOCUMENTS

WO    WO 2007/084285    6/2007

OTHER PUBLICATIONS

International Search Report for PCT Application No. PCT/IL2020/050544 maile on Jul. 30, 2020.

* cited by examiner

*Primary Examiner* — Ariana Zimbouski
*Assistant Examiner* — Yasniary De La Caridad Morales
(74) *Attorney, Agent, or Firm* — PEARL COHEN ZEDEK LATZER BARATZ LLP

(57) ABSTRACT

A nipple implant assembly comprises a lower base portion with a lower base tip, an upper base portion with an upper base tip, a mesh support structure located between the lower and the upper base, and a slot extending from the outer circumference of the lower base, the mesh and the upper base portions to the lower tip and the upper tip. A removable clip connects the slot edges to keep the opening of the slot at a defined size.

20 Claims, 5 Drawing Sheets

CROSS SECTION A-A

CROSS SECTION B-B

IMPLANTABLE NIPPLE

CROSS-REFERENCE TO RELATED APPLICATIONS

This application is a National Stage Application under 35 U.S.C. § 371 of U.S. Patent Application No. PCT/IL2020/050544, filed May 19, 2020, entitled IMPLANTABLE NIPPLE, which claims the benefit under 35 U.S.C. § 119(e) of U.S. Provisional Application No. 62/850,555, filed May 21, 2019 which is hereby incorporated by reference.

BACKGROUND OF INVENTION

Traditionally, in the case of breast cancer, the whole breast is removed and thereafter it is reconstructed, mostly using silicone or saline breast inserts. Currently, the breast inserts do not comprise a nipple. So a nipple implant has to be implanted separately.

Furthermore nipple inversion is a common problem. Flat nipples and nipple inversion at women's breasts is a very common phenomena. Furthermore it is known that women with regular nipples are unhappy with their look. Women share a common desire of improving their nipples' shape and appearance by a cosmetic plastic procedure.

SUMMARY OF THE INVENTION

The present invention, in some embodiments thereof, relates to implantable nipples and implantable nipples with an integrated areola also denoted throughout the description of embodiments of the present invention 'nipple assembly implant', more particularly, but not exclusively, to components to be implanted in a human breast. Nipples and nipples with areola implantable components and a simple implantation procedures, in which a prefabricated nipple and/or nipple with integrated areola is implanted in a human's breast.

In some embodiments a nipple implant assembly is presented comprising a lower base portion comprising a lower base tip, an upper base portion comprising an upper base tip, a mesh support structure located between the lower and the upper base, a slot extending from the outer circumference of the lower base, the mesh and the upper base portions to the lower tip and the upper tip and a removable clip adapted to connect the slot edges to keep the opening of the slot at a defined size.

In some embodiments a nipple implant assembly is presented comprising a lower base portion comprising a lower base tip, an upper base portion comprising an upper base tip, a mesh support structure located between the lower and the upper base, a slot extending from the outer circumference of the lower base, the mesh and the upper base portions to the lower tip and the upper tip. The upper base tip comprises a hollow space adapted to be filled with liquid or jell.

According to some embodiments of the invention, including, for example, any of the embodiments described herein, the nipple and/or nipple with integrated areola implant base may consist of an opening slot extending from the base circumference to center of the implant in a wedge shape. The opening allows the insertion of the implant in its place without interfering with the breast nerves and milk ducts and milk supply system to the nipple and/or nipple with integrated areola.

According to some embodiments of the invention, including, for example, any of the embodiments described herein, the nipple implant and/or nipple implant with integrated areola base may consist of a clip that is adapted to keep the size of the opening in the wedge slot after the implant is placed in its place those giving the structure an enhanced force to hole its shape for a long period of time.

According to some embodiments of the invention, including, for example, any of the embodiments described herein, the nipple implant and/or nipple implant with integrated areola base consists a hollow space adapted to be filled with liquid emulsion such as salt water emulsion or saline or with jell.

According to some embodiments of the invention, including, for example, any of the embodiments described herein, the nipple implant and/or nipple implant with integrated areola base is provided as integral part of a breast insert or assembled on breast insert by bonding materials such as biomedical glue or by mechanical means such as ultrasound.

According to an aspect of some embodiments of the present invention, including, for example, any of the embodiments described herein, there is provided a nipple implant and/or nipple implant with integrated areola consisting of resilient material such as Silicone, plastic or polymer configured to be implanted under the existing nipple and areola skin and may be coincided with the natural nipple and areola. The implant thus retains the natural nipple and areola in a projecting manner stretches the nipple natural skin and gives it a new fresh look while maintaining the softness of a human's tissue.

According to some embodiments of the invention, including, for example, any of the embodiments described herein, the implant consists of a supporting structure, or skeleton, having a mesh-like skeleton form, optionally built from a memory shape material such as Nitinol, Titanium Alloy or similar material casted in or coated by a soft and flexible biomedical material such as Silicone, plastic or polymer. The implant skeleton may sustain its dimensions and shape at the body constant temperature while providing the necessary force for pushing the existing inverted nipple out to take the form and look of a natural and regular nipple, while the soft material covering the skeleton is adapted to follow the changes in form of the implant skeleton.

According to some embodiments of the invention, including, for example, any of the embodiments described herein, the implant consists of a mesh configure to be built from a shape memory and/or a temperature memory material and may be covered with softer material such as Silicone, plastic or other polymer. Thus, the configured built enhancing the hold of the implantable in its position under the breast skin preventing a movement, distortion or a distension of the implanted nipple and areola in the breast.

According to some alternative embodiments of the invention, including, for example, any of the embodiments described herein, the implant consists of a support skeleton shaped as a mesh or other fixture made of hard plastic, Silicone or Polymeric material. This internal fixture is made of a soft plastic, Silicone or Polymeric material similarly to the casting of a metal skeleton described above.

According to some embodiments of the invention, including, for example, any of the embodiments described herein, the implant base is shaped as flat or hemisphere structure and comprises openings that allow natural breast tissue to grow into the opening and thereby enabling a solid bonding of the implant into the existing nipple, areola and breast tissues.

According to some embodiments of the invention, including, for example, any of the embodiments described herein, the nipple implant and/or nipple implant with integrated areola and/or a nipple base consist of supporting biomedical material, for example a metal such as medical grade stainless steel, Nitinol, Titanium alloy or similar materials.

According to some embodiments of the invention, including, for example, any of the embodiments described herein, the thickness of the implantable base may vary between 0.1 mm to 25 mm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 1A depicts a schematic illustration of a nipple implant general assembly with wedge opening, according to embodiments of the invention;

Figure 1B:
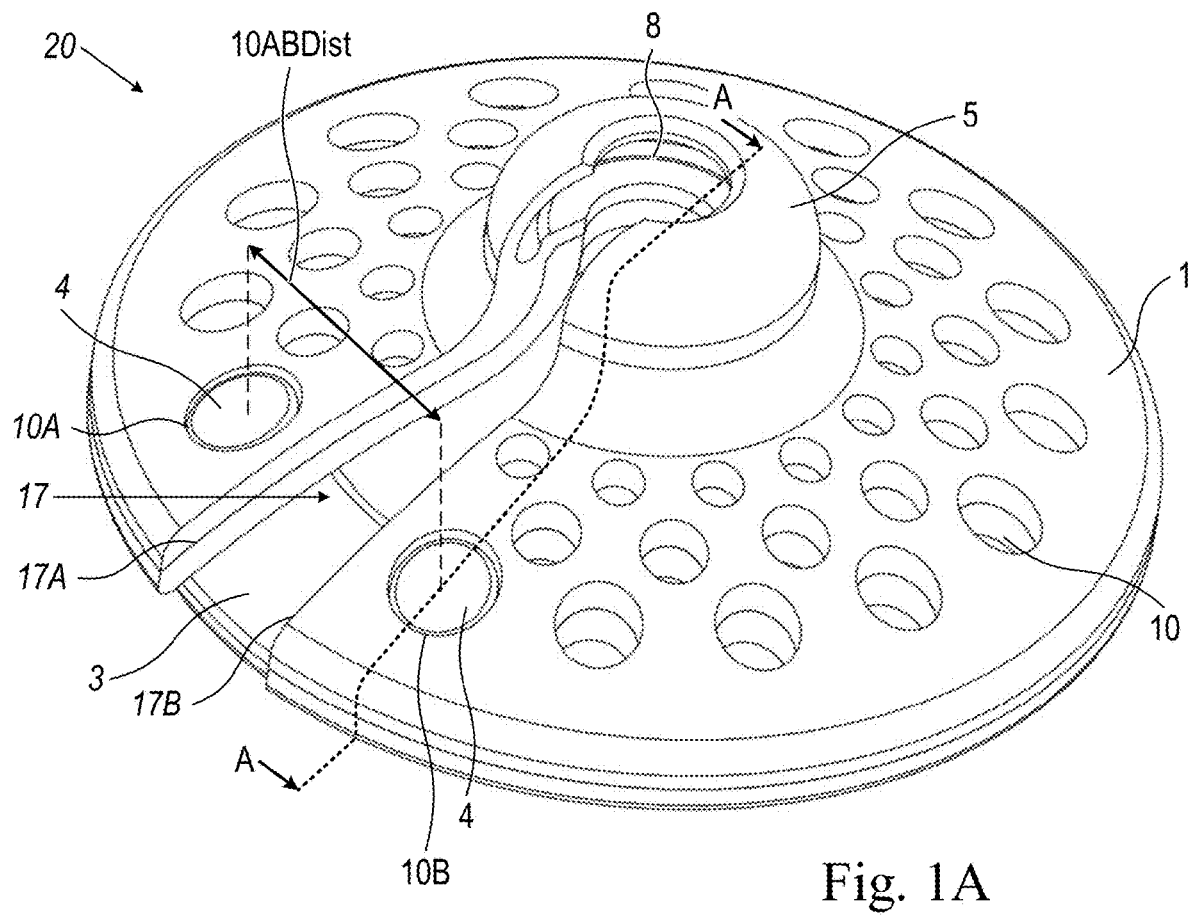
FIG. 1B depicts a schematic partial cross section of the nipple implant assembly of FIG. 1A, according to embodiments of the invention.
Figure 1B:
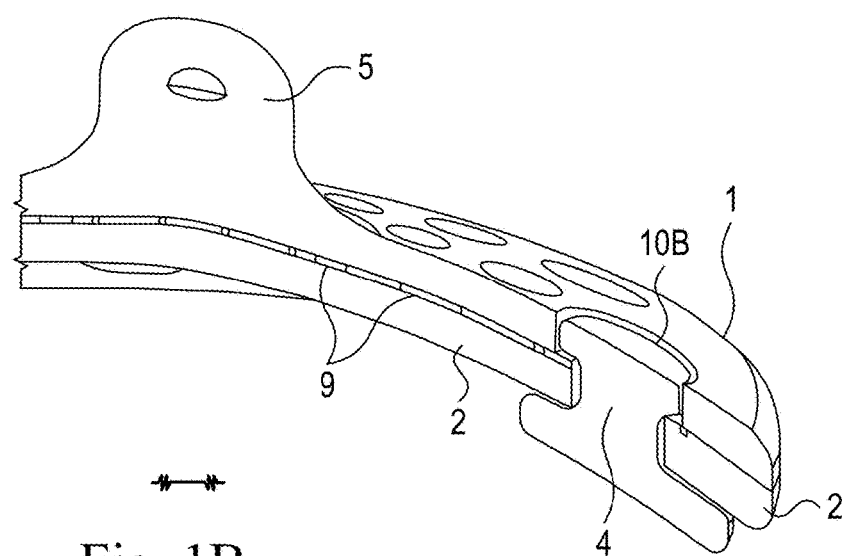

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention.

Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies 20 regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

A broad aspect of some embodiments of the invention relates to nipple and/or nipple with integrated areola—commonly denoted 'nipple assembly implant'—configurations. In some embodiments of the invention the implant may consist of a base with a nipple and/or nipple with integrated areola tip attached to it where the base and the nipple and/or nipple with integrated areola 30 may be made from Silicone or other plastic or Polymeric material. The implant may be manufactured in molding technology known in the art. In some embodiments the implant may be configured to be the tip alone. In some embodiments, the implant may be enhanced with a supporting metal construction made of biomedical compatible material giving the implant strength and ability to sustain the prefabricated shape for a long duration through a large range of body rapidly changing parameters, such as body temperature. In some embodiments the implant may be of formed of a metal mesh or helix spring. The metal mesh may be covered with biomedical compatible Silicone, plastic or Polymeric material film. The mesh and the cover film together may give the implant strength and smoothness.

It should be noted that all materials presented here are biocompatible materials suitable for using in the body such as Nitinol and/or stainless-steel grade 316 or other materials known in the art. An aspect of some method of the invention relates to the insertion of the implant in the breast that may be done under local anesthesia. The relatively small implant size, the flexibility yet having significant strength allow for simple clinical procedure. It is to be understood that the invention is not necessarily limited in its application to the details of construction and the arrangement of the components and/or methods set forth in the following description and/or illustrated in the drawings. The scope of the invention extends to other embodiments or may be practiced or carried out in various other ways.

Reference is made to FIG. 1A which is a schematic illustration of a nipple implant assembly 20 with wedge opening and to FIG. 1B, which is a schematic partial cross section of the nipple implant assembly of FIG. 1A, according to embodiments of the invention. Nipple implant assembly 20 consists of lower base 2 and upper base 1 is presented. The lower base 2 and the upper base 1 may be bonded with biocompatible glue or other measures of bonding such as a mechanical bonding of ultrasound waves bonding. In between the lower base 2 and the upper 1 base a mesh 9 (which is seen in detail in FIG. 5) may be inserted. During assembly of nipple implant assembly 20 the mesh 9 is first assembled over the lower base 2 and then the upper base 1 is assembled over the mesh 9 and is glued or bonded.

Furthermore nipple implant assembly 20 consists of upper base tip 5 and a space or cavity 8 made in the tip structure. The cavity 8 may be filled with saline or saltwater emulsion. The addition of the emulsion in the cavity 8 makes the tip softer.

The lower base 2 and the upper base 1 consist of many holes 10, the holes made in lower base 1 coincide with corresponding holes made in upper base 2. When lower base 1 and upper base 2 are assembled two of each corresponding pairs of holes which coincide with one other make a one trough hole 10. The lower base 2 and the upper base 1 consist also of an opening (or slot) 17 in a form of a wedge shape extending from the outer circumference of lower and upper bases 2 and 1 to the center of upper base tip 5.

Figure 2:
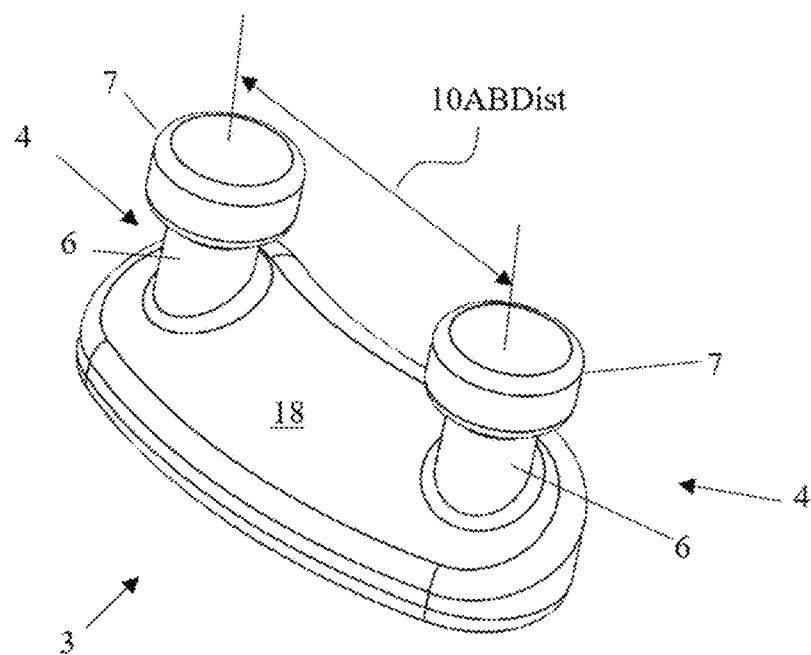
FIG. 2 presents a schematic illustration of an implant lock clip structure, according to embodiments of the invention.

The distance between two lips 17A, 17B of opening 17 may be kept constant (against its optional broadening after the implant is inserted) with clip 3, which is described in detail with respect to FIG. 2. Pins 4 of clip 3 may be inserted through corresponding holes 10A, 10B after to prevent the lips from opening, thereby holding opening 17 in constant open angle state. The upper base 1 and lower base 2 may generally be made from plastic flexible biocompatible materials such as silicon.

Reference is made to FIG. 2, presenting a schematic illustration of clip 3, according to embodiments of the invention. The clip 3 consists of base 18 and two pins 4 extending from base 18. The pins 4 consist of pin base 6 and pin top 7. The diameter of pin base 6 and of pin 7 may be between 1 mm to 10 mm where the diameter of top 7 may be larger than that of pin base 6. The distance 3Dist between the centers of pins 4 substantially equals to the distance 10ABDist between holes 10A and 10B. The pins 4 may be inserted through holes 10A, 10B, holes 12 holes 11 and holes 13 (seen in FIGS. 1A, 1B, 3, 4 and 5 respectfully) of lower base 1 and upper base 2. Once clip 3 is inserted in place and pins 4 are properly inserted in the respective holes, the outer circumference of the wedge shape opening 17 is securely kept in the desired measure. The insertion of clip 3 is usually done after the nipple impalpable assembly 20 is placed in its place in the breast body thereby it retains a force to prevent further opening of the wedge shape 17 and giving the impalpable nipple 20 a better and stronger hold of the body. The clip may be made of resilient flexible plastics such as silicon or reinforced silicon or biocompatible metal such as Stainless steel or Nitinol.

Figure 3:
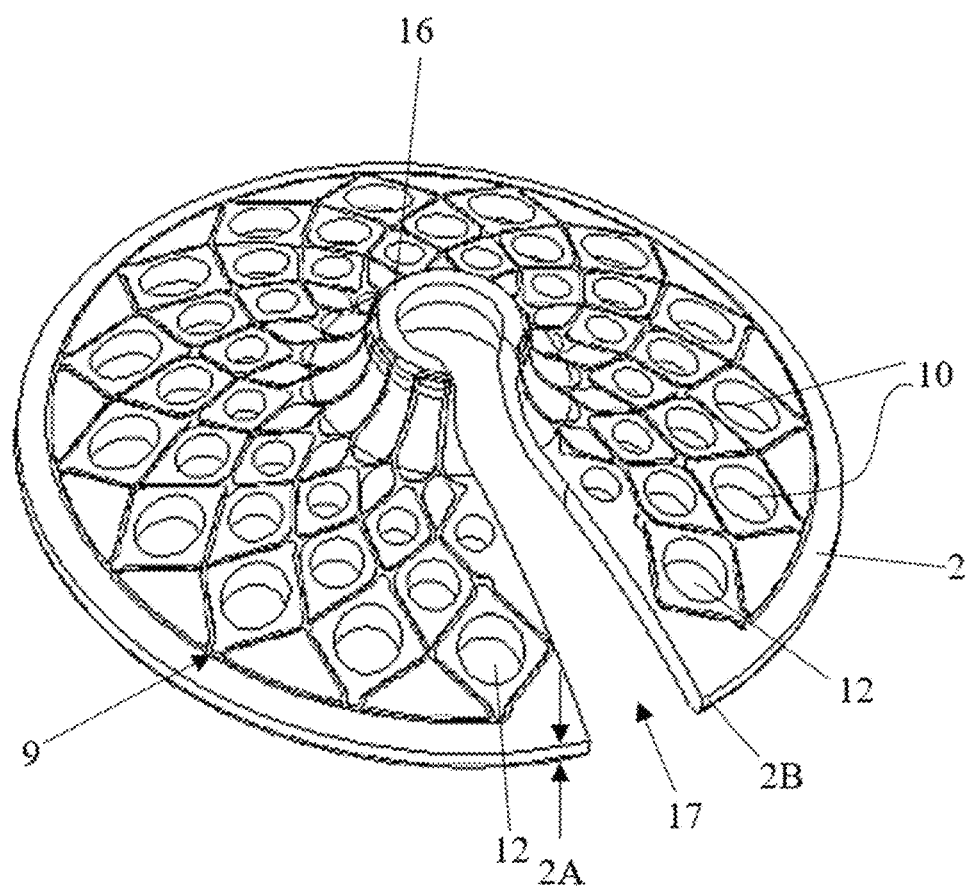
FIG. 3 presents in detail the lower base of an implant assembly, according to embodiments of the invention.

FIG. 3, to which refence is made now, presents in detail the lower base 2 of implant assembly 20, according to embodiments of the invention. The lower base 2 is formed as a circular body with a diameter between 0.5 cm and 10 cm and base thickness 2A of between 0.1 cm and 1 cm. The circular body consists of many holes 10 in varying diameters ranging between 1 mm to 10 mm. The holes 10 purpose is to let the breast tissue organs grow into and through the holes and provide the nipple implant a fixed hold in the breast body after the nipple was placed by the physician.

The base 2 also consists of a longitudinal opening 17 (or slot) in a form of a wedge. The opening 17 stretches from the outer circumference 2B of the base 2 to the tip 16. The size of wedge 17 opening size is between 1 mm and 40 mm at outer circumference of the opening getting narrower toward lower base tip 16. The opening purpose is to enable insertion of the nipple implant into its place in the breast body without the necessity to cut through the breast ducts, nerves and vessels.

Two holes 12 are adapted to accommodate pins 4 and are undersized in diameter compared to the diameter of top 7 of pin 4 in order to create pressure to hold the pin 4 in place when inserted to holes 12. Mesh 9 (another embodiment of a mesh is seen in detail in FIG. 5) is an independent component and is shown here for convenience of the explanation. While the nipple implant 20 is assembled the mesh 9 is placed as shown over the base 2 and the lower base tip 16 so both—base 2 and lower base tip 16—are covered by mesh 9. Mesh 9 may provide strengthening skeleton to the assembled nipple implant for maintaining its form while providing high level of flexibility.

Figure 4:
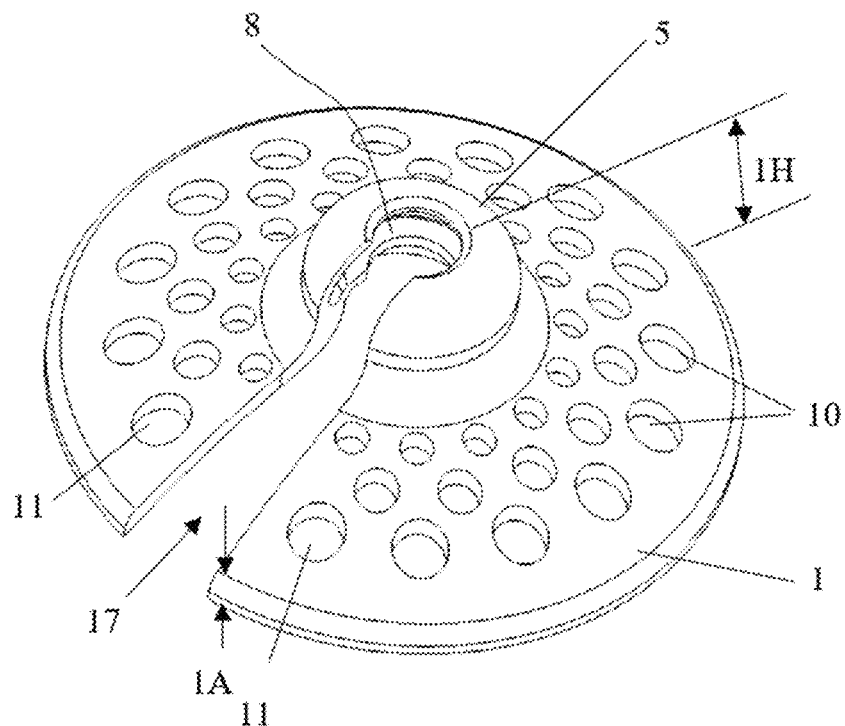
FIG. 4 presents an upper base of a nipple implant assembly in detail, according to embodiments of the invention.

FIG. 4, to which reference is now made, presents upper base 1 of a nipple implant assembly in detail, according to embodiments of the invention. The base is formed as a circular body with a diameter between 0.5 cm and 10 cm and skin thickness 1A of between 0.1 mm and 1 cm. The height 1H may be between 0.5 cm and 4 cm. The body consists of many holes 10 in a diameter varying between 1 mm to 10 mm. The holes purpose is to let the breast tissue organs grew into and through the holes and give the nipple implant a fixed hold in the breast body after the nipple was placed by the physician.

The upper base 1 consists the same size and same location of opening wedge 17 as in lower base 2. When the two parts, upper base 1 and lower base 2, are assembled the openings coincide with each other. So are holes 10A, 10B, 11, 12 and 13 coinciding respectively, thereby enabling pins 4 to be inserted through. The upper base 1 consists of a tip 5 with a space/cavity 8 in it. When upper base 1 is assembled over lower base 2 with the mesh 9 between them, the space of cavity 8 is sealed. The cavity is then may be filled by injection of saline or salt water to give the nipple 8 a softer filing.

Figure 5:
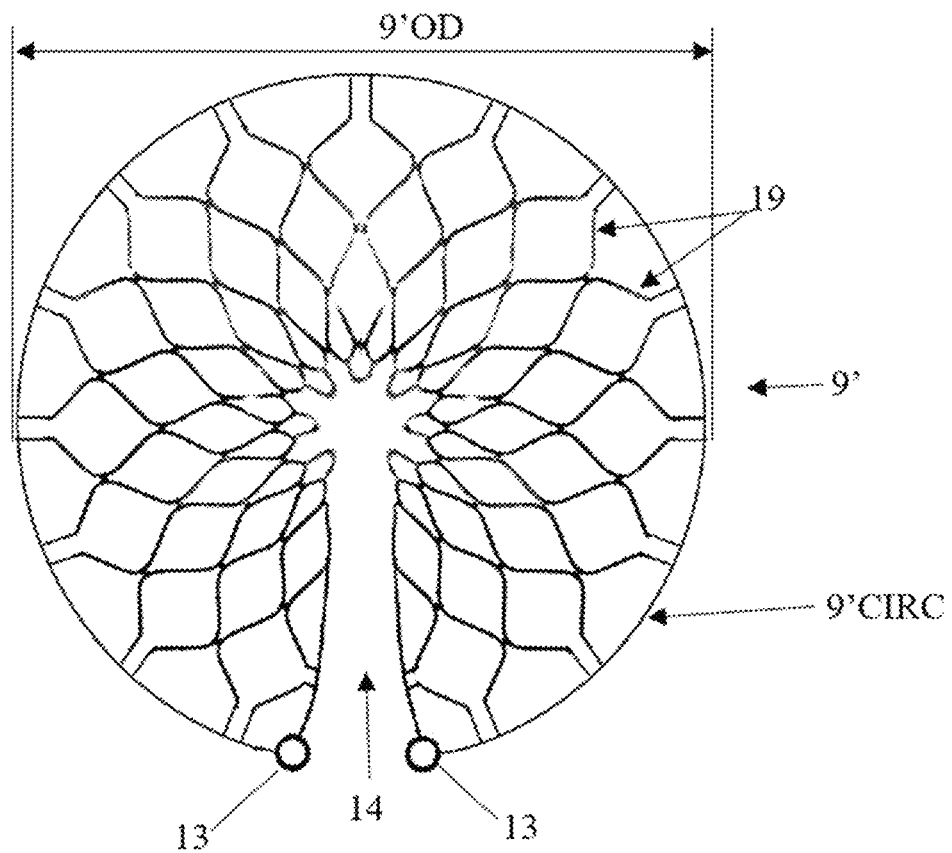
FIG. 5 presents in detail the structure of a mesh according to embodiments of the invention.

FIG. 5, to which reference is made now, presents in detail the structure of the mesh 9', according to embodiments of the invention. The mesh 9' may be similar to mesh 9 of FIG. 3 with few differences. Mesh 9' may be made from wires 19 made of metal such as Nitinol with or another metal without shape memory capabilities or from various Stainless-steel materials. The wire diameter may be 0.1-2 mm. The wire may have a rectangular or other cross section shape with equivalent cross section area dimensions. The outer diameter 9'OD of mesh 9' coincides with the outer diameter of lower base 2 and upper base 1 of the assembly.

The pattern of the mesh is usually of honeycomb-like which gives the assembled implant nipple 20 an enhanced strength and capabilities to keep its manufactured mechanical dimensions and stability for a long period of time after implanted in the body.

The mesh consists of an opening 14 in the shape of wedge adapted to coincide in dimensions and location with the openings of upper and lower base 1 and 2 respectively. It also consists of two holes 13 designed to let pins 4 free passage when inserted and provide stable hold against broadening of nipple assembly 20. In some embodiments mesh 9' may comprise a circumference ring 9'CIRC that encircles mesh 9' extending from first hole 13 to the second hole 13.

Figure 6A:
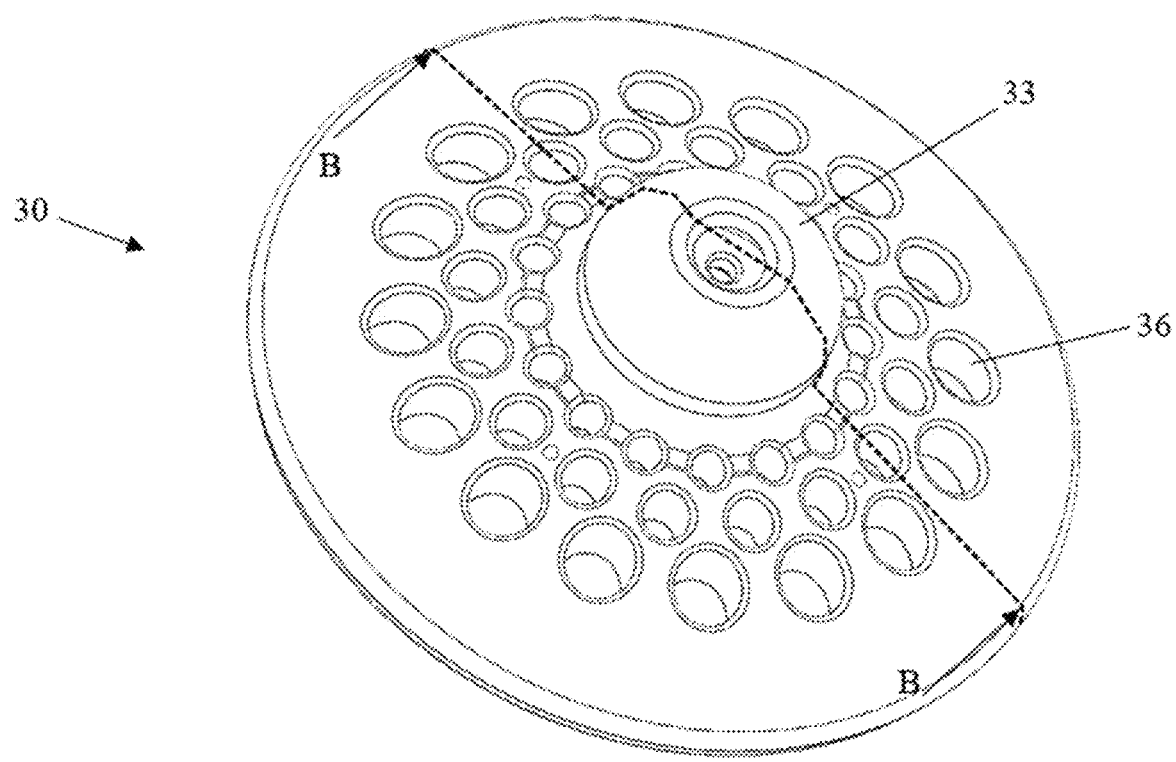
FIG. 6A is a schematic illustration of implant nipple assembly 30 without an opening, according to embodiments of the invention.
Figure 6B:
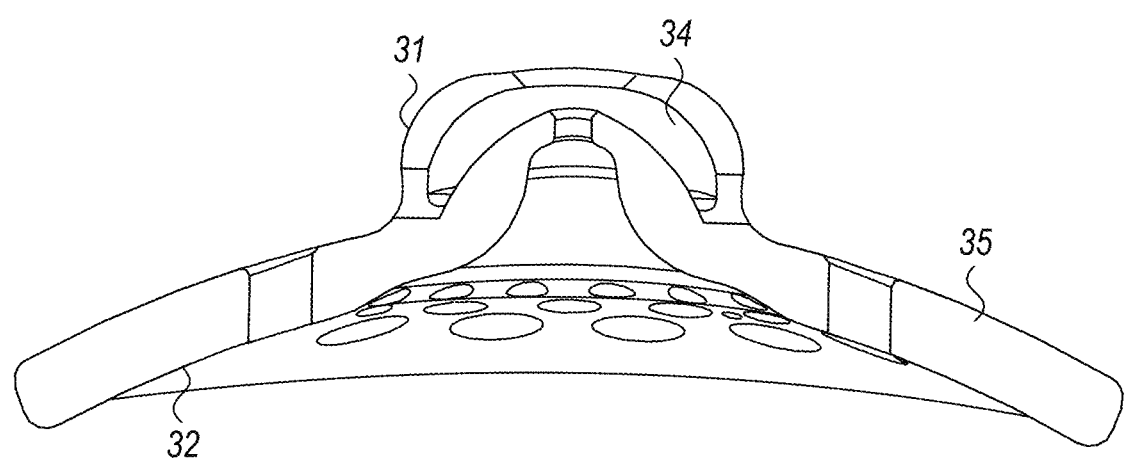
FIG. 6B is a schematic Cross-section illustration of a nipple implant assembly of FIG. 6A, according to embodiments of the invention.

Reference is made now to FIG. 6A which is a schematic illustration of implant nipple assembly 30, and to FIG. 6B which is a cross-section of FIG. 6A along line B-B, both presenting a nipple implant assembly 30 without an opening wedge, according to embodiments of the present invention. The materials and mechanical dimensions of corresponding components in assembly 30 are similar to those of nipple assembly 20. The assembly bonding procedure of the components is also similar to those in 20.

Implant assembly 30 consists of lower base 32 and upper base 31 with mesh 35 between them. The assembly 30 consists of a tip 33 with cavity/space 34. The space/cavity 34 may be filled by injection with saline or water salt emulsions or other soft materials. The implant assembly 30 also consists of holes 36 that go through lower and upper base 32 and 31 respectively allowing for breast organ tissues penetrate trough for better holding and location stability after implanting.

Figure 7:
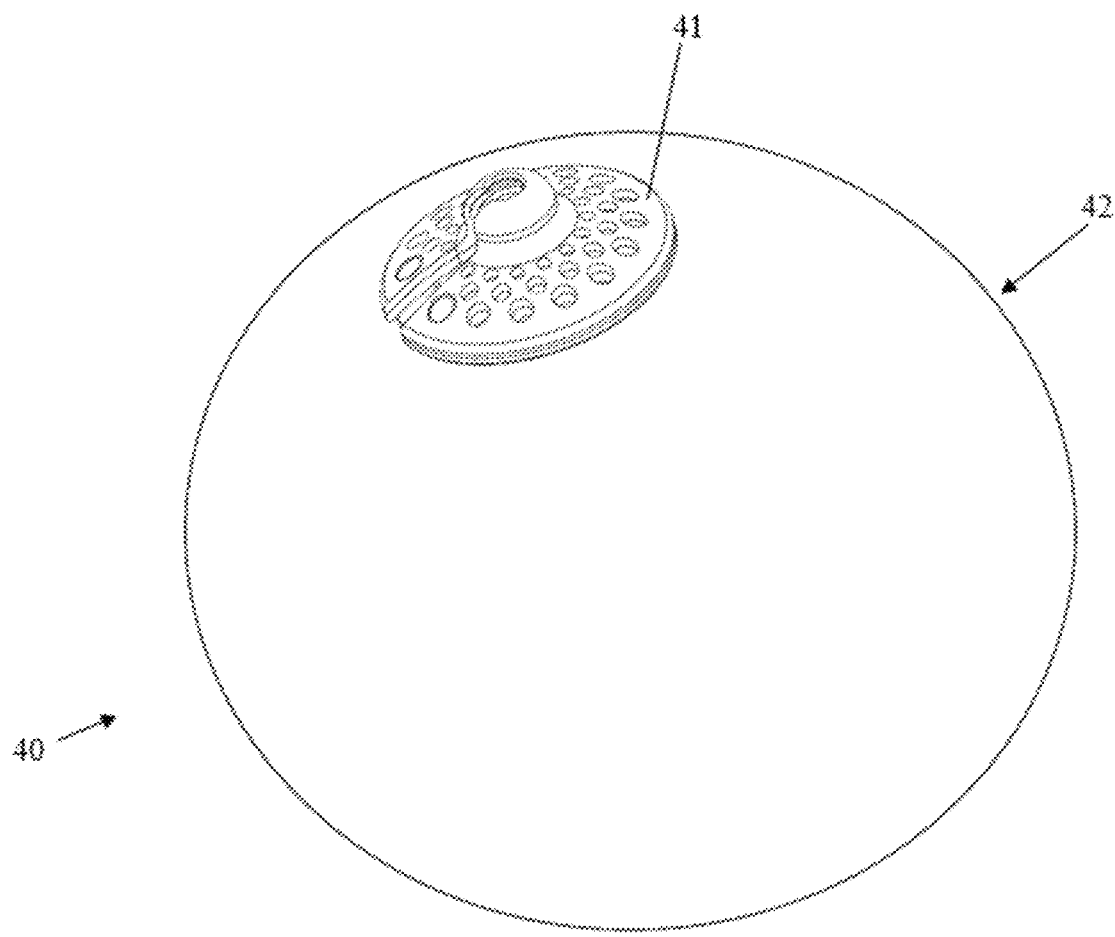
FIG. 7 presents a general assembly of breast silicon insert with a nipple implant according to embodiments of the present invention.

FIG. 7, to which reference is now made, presents a general assembly of breast silicon insert with a nipple implant 42, according to embodiments of the present invention. Nipple implant assembly 41 may be similar to nipple assembly 20 or 30, assembled as is known in the market or specially designed breast silicon insert 40 by bonding process of biological glue or other mechanical means such as ultrasound waves.

What I claimed is:

1. A nipple implant assembly comprising:
   a lower base portion comprising a lower base tip;
   an upper base portion comprising an upper base tip;
   a mesh support structure located between the lower base portion and the upper base portion;
   a slot extending from an outer circumference of the lower base portion, the mesh support structure, and the upper base portion, to the lower base tip and the upper base tip; and
   a removable clip adapted to connect edges of the slot to keep an opening of the slot at a defined size.

2. The nipple implant assembly of claim 1, wherein the upper base tip consists of a hollow space.

3. The nipple implant assembly of claim 2, wherein the hollow space is adapted to be filled with liquid or gel.

4. The nipple implant assembly of claim 1, wherein the mesh support structure is made of memory-shape metal.

5. The nipple implant assembly of claim 1, wherein the mesh support structure is made of nitinol.

6. The nipple implant assembly of claim 1, wherein the mesh support structure is made of stainless steel.

7. The nipple implant assembly of claim 1, wherein the lower base portion, upper base portion, and mesh support structure are made of bio-compatible polymer.

8. The nipple implant assembly of claim 7, wherein the lower and upper base portions and the mesh support structure are made of silicone.

9. The nipple implant assembly of claim 1, wherein the slot is adapted to allow insertion of a structure extending from the nerves, the milk ducts and the milk supply system of a woman's breast through the slot without having to cut or disconnect the breast's natural nipple and areola from the nerves, the milk ducts and the milk supply system of the woman's breast.

10. The nipple implant assembly of claim 1, wherein the mesh support structure is made of a non-metallic material.

11. The nipple implant assembly of claim 1, wherein the lower base portion and the upper base portion comprise holes.

12. A nipple implant assembly comprising:
    a lower base portion comprising a lower base tip;
    an upper base portion comprising an upper base tip; and
    a mesh support structure located between the lower base portion and the upper base portion;
    wherein said upper base tip consists of a hollow space.

13. The nipple implant assembly of claim 12, wherein the upper base tip is configured to enable the hollow space to be filled with liquid or gel.

14. The nipple implant assembly of claim 12, wherein the mesh support structure is made of memory-shape metal.

15. The nipple implant assembly of claim 12, wherein the mesh support structure is made of nitinol.

16. The nipple implant assembly of claim 12, wherein the mesh support structure is made of stainless steel.

17. The nipple implant assembly of claim 12, wherein the upper and lower base portions and mesh support structure are made of bio-compatible polymer and/or made of silicone.

18. The nipple implant assembly of claim 12, wherein the mesh support structure is made of a non-metallic material.

19. The nipple implant assembly of claim 12, wherein the lower base portion and upper base portion comprise holes.

20. An implantable assembly comprising:
    the nipple implant assembly of claim 12; and
    a breast silicone insert.

* * * * *